(12) United States Patent
Sekine

(10) Patent No.: US 12,178,411 B2
(45) Date of Patent: Dec. 31, 2024

(54) FECES COLOR DETECTION DEVICE

(71) Applicants: SETECH CO., LTD., Kanagawa (JP);
TOTO LTD., Kitakyushu (JP)

(72) Inventor: Hirokazu Sekine, Kanagawa (JP)

(73) Assignees: SETECH CO., LTD., Kanagawa (JP);
TOTO LTD., Kitakyushu (JP)

( * ) Notice: Subject to any disclaimer, the term of this patent is extended or adjusted under 35 U.S.C. 154(b) by 0 days.

(21) Appl. No.: 18/489,187

(22) Filed: Oct. 18, 2023

(65) Prior Publication Data

US 2024/0057982 A1 Feb. 22, 2024

Related U.S. Application Data

(60) Division of application No. 16/572,990, filed on Sep. 17, 2019, now Pat. No. 11,819,198, which is a
(Continued)

(30) Foreign Application Priority Data

Jun. 18, 2014 (JP) ................................. 2014-125844

(51) Int. Cl.
*A61B 10/00* (2006.01)
*A47K 13/24* (2006.01)
(Continued)

(52) U.S. Cl.
CPC ............ *A61B 10/0038* (2013.01); *A61B 5/00* (2013.01); *A61B 5/6891* (2013.01); *E03D 9/00* (2013.01);
(Continued)

(58) Field of Classification Search
None
See application file for complete search history.

(56) References Cited

U.S. PATENT DOCUMENTS

| | | | |
|---|---|---|---|
| 4,636,474 A | 1/1987 | Ogura et al. | |
| 4,682,040 A | 7/1987 | Hohki et al. | |

(Continued)

FOREIGN PATENT DOCUMENTS

| | | | |
|---|---|---|---|
| CN | 1459634 A | 12/2003 | |
| CN | 1679443 A | 10/2005 | |

(Continued)

OTHER PUBLICATIONS

International Search Report dated Aug. 25, 2015 from corresponding International Patent Application No. PCT/JP2015/066420; 2 pgs.

(Continued)

*Primary Examiner* — Neil N Turk
(74) *Attorney, Agent, or Firm* — Maier & Maier, PLLC

(57) ABSTRACT

A plurality of color sensing sections are attached to a toilet seat so as to test a health state or a fecal occult blood portion every time by capturing the feces surface color during defecation. Before feces which have been excreted from a body sink into a water-seal portion, the circumference of the feces is optically captured to detect the color of the surface of the feces. By monitoring changes in color, the health state of the defecator is monitored. In particular, by checking the presence/absence of an occult blood portion, the present invention assists in early detection of colorectal cancer and allows a fecal occult blood test to be performed in a hygienic manner without burdening the user.

2 Claims, 7 Drawing Sheets

Related U.S. Application Data continuation of application No. 15/319,473, filed as application No. PCT/JP2015/066420 on Jun. 7, 2015, now abandoned.

(51) Int. Cl.
*A47K 13/30* (2006.01)
*A61B 5/00* (2006.01)
*E03D 9/00* (2006.01)
*G01N 21/31* (2006.01)
*G01N 21/84* (2006.01)
*G01N 33/483* (2006.01)

(52) U.S. Cl.
CPC ........... *G01N 21/314* (2013.01); *G01N 21/84* (2013.01); *G01N 33/4833* (2013.01); *A47K 13/24* (2013.01); *A47K 13/30* (2013.01); *G01N 2021/3144* (2013.01)

(56) References Cited

U.S. PATENT DOCUMENTS

| | | | |
|---|---|---|---|
| 5,563,809 | A | 10/1996 | Williams et al. |
| 5,726,595 | A | 3/1998 | Lin et al. |
| 9,828,755 | B1 | 11/2017 | Clements |
| 9,867,513 | B1 | 1/2018 | Hall et al. |
| 2005/0228242 | A1 | 10/2005 | Kawamura et al. |
| 2006/0155580 | A1 | 7/2006 | Kawamura |
| 2006/0167383 | A1 | 7/2006 | Kieturakis et al. |
| 2007/0122916 | A1 | 5/2007 | Oleynik |
| 2008/0300651 | A1 | 12/2008 | Gerber et al. |
| 2011/0083264 | A1* | 4/2011 | Gunderson ............ A47K 17/00 4/661 |
| 2012/0116159 | A1 | 5/2012 | Mizuyoshi et al. |
| 2013/0228675 | A1 | 9/2013 | Chen et al. |
| 2014/0015505 | A1 | 1/2014 | George-Kelso et al. |
| 2014/0147924 | A1 | 5/2014 | Wheeldon et al. |
| 2014/0151558 | A1 | 6/2014 | Bortot et al. |

FOREIGN PATENT DOCUMENTS

| | | | |
|---|---|---|---|
| CN | 101442927 A | 5/2009 | |
| CN | 102352649 A | 2/2012 | |
| CN | 102594999 A | 7/2012 | |
| CN | 102809976 A | 12/2012 | |
| CN | 103067723 A | 4/2013 | |
| CN | 103149212 A | 6/2013 | |
| CN | 202969531 U | 6/2013 | |
| CN | 203136283 U | 8/2013 | |
| CN | 103398946 A | 11/2013 | |
| CN | 103411676 A | 11/2013 | |
| CN | 103535116 A | 1/2014 | |
| CN | 103546029 A | 1/2014 | |
| JP | H05228182 A | 9/1993 | |
| JP | H05332939 A | 12/1993 | |
| JP | H07216963 A | 8/1995 | |
| JP | H08299285 A | 11/1996 | |
| JP | H09018888 A | 1/1997 | |
| JP | H0978656 A | 3/1997 | |
| JP | H10031016 A | 2/1998 | |
| JP | H10260182 A | 9/1998 | |
| JP | H10339728 A | 12/1998 | |
| JP | H1183745 A | 3/1999 | |
| JP | H11342115 A | 12/1999 | |
| JP | 2000232964 A | 8/2000 | |
| JP | 2002266407 A | 9/2002 | |
| JP | 2005013244 A | 1/2005 | |
| JP | 2005037278 A | 2/2005 | |
| JP | 2006061296 A | 3/2006 | |
| JP | 2006132948 A | 5/2006 | |
| JP | 2007252805 A | 10/2007 | |
| JP | 2008081929 A | 4/2008 | |
| JP | 200952943 A | 3/2009 | |
| JP | 2009270951 A | 11/2009 | |
| JP | 2009271038 A | 11/2009 | |
| JP | 2010014586 A | 1/2010 | |
| JP | 4516018 B2 | 8/2010 | |
| JP | 2011010998 A | 1/2011 | |
| JP | 201324613 A | 2/2013 | |
| JP | 2013082267 A1 | 6/2013 | |
| JP | 2013212247 A | 10/2013 | |
| KR | 1020120073919 A | 7/2012 | |
| KR | 20130016995 A | 2/2013 | |
| KR | 101368144 B1 | 2/2014 | |
| TW | 201117758 A1 | 6/2011 | |
| WO | 2013047565 A1 | 4/2013 | |

OTHER PUBLICATIONS

Japanese Office Action dated Apr. 6, 2015 from corresponding Japanese Patent Application No. JP2014-125844; 6 pgs.
Japanese Office Action dated Aug. 5, 2015 from corresponding Japanese Patent Application No. JP2014-125844; 4 pgs.
Extended European Search Report dated Jun. 14, 2017, including the Supplementary European Search Report and the European Search Opinion, in connection with corresponding EP Application No. 15808863.3 (8 pgs.).
Office Action issued on Jul. 30, 2018 in corresponding Chinese Application No. 201580032542.X; 13 pages including English-language translation.
Chinese Office Action issued on Feb. 2, 2021, in connection with corresponding CN Application No. 201910277924.9 (19 pp., including machine-generated English translation).
Office Action issued on Mar. 26, 2021 in corresponding Chinese Office Action 201910277480.9; 11 pages including English-language translation.
Chinese Office Action issued on Aug. 4, 2021, in connection with corresponding CN Application No. 201910277924.9 (14 pp., including machine-generated English translation).
Liang Bing, "Design of a high-speed line array CCD image acquisition system" Chinese Doctoral Dissertations & Master's Theses Full-text Database Information Science and Technology. vol. 4. Apr. 15, 2011. 6 pages. Partial machine-generated English translation provided.
Ma Huai-Hsiang, et al. Digital Sensors. Engineering Testing Techniques, China National University of Science and Technology Press. Feb. 28, 2014. 8 pages. Partial machine-generated English translation provided.
Office Action issued on Dec. 7, 2021, in connection with corresponding Chinese Application No. 201910277480.9 (11 pp., including machine-generated English translation).
Office Action issued on Jun. 15, 2022, in connection with corresponding Chinese Application No. 201910277924.9 (18 pp., including machine-generated English translation).
Office Action issued on Jun. 20, 2022, in connection with corresponding Chinese Application No. 201910277480.9 (10 pp., including machine-generated English translation).

* cited by examiner

[Fig. 1]
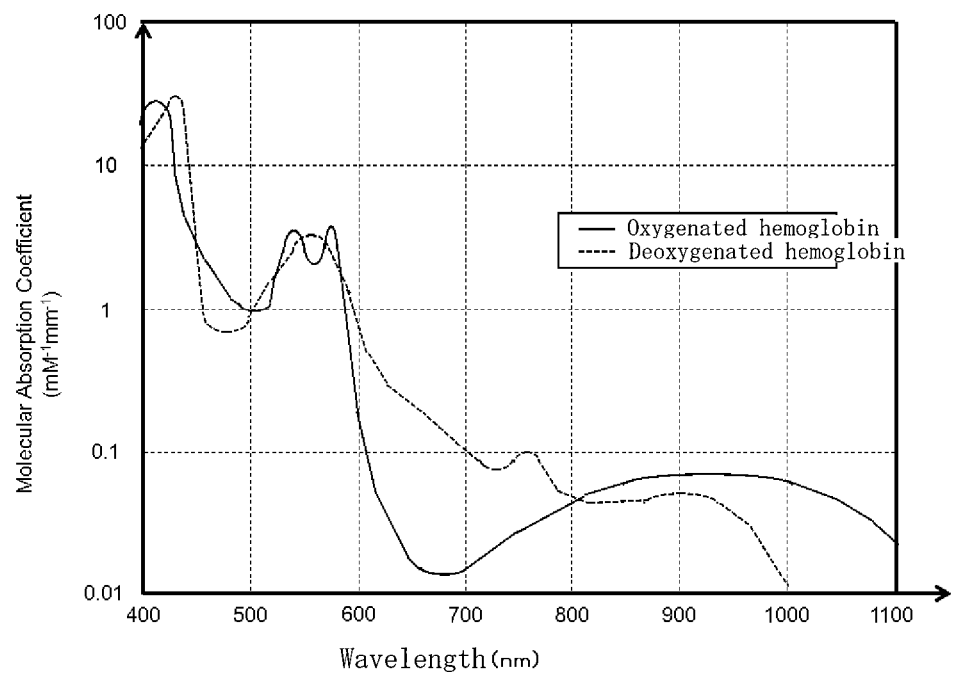
[Fig. 2]
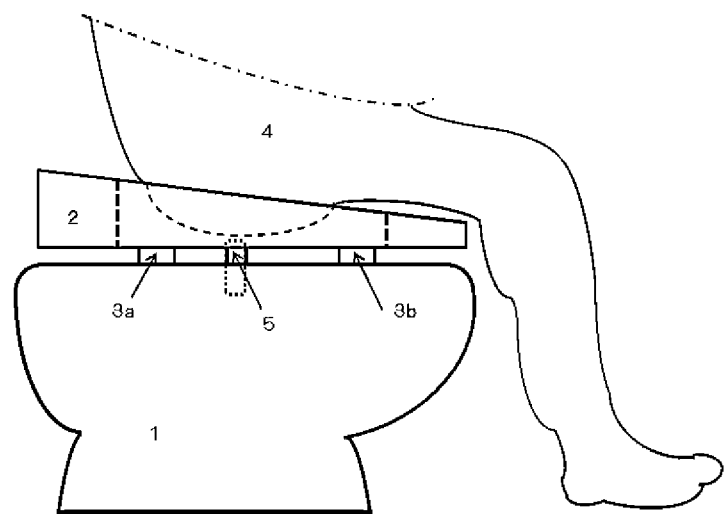

[Fig. 3(a)]
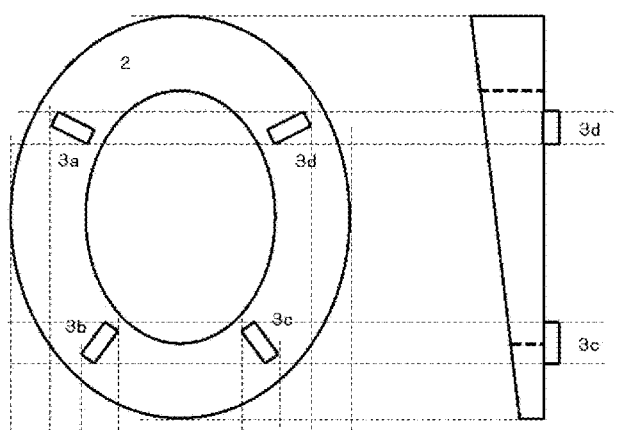
[Fig. 3d]
[Fig. 3(b)]
[Fig. 3(c)]
[Fig. 4]
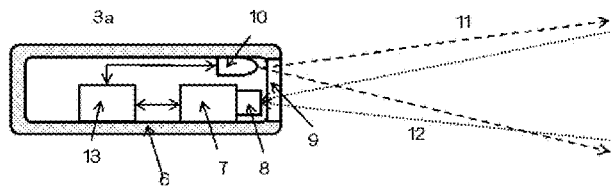
[Fig. 5]
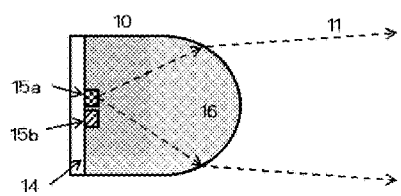
[Fig. 6]
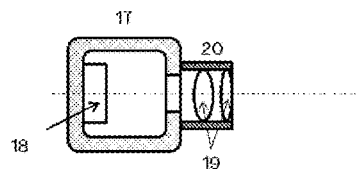
[Fig. 7]
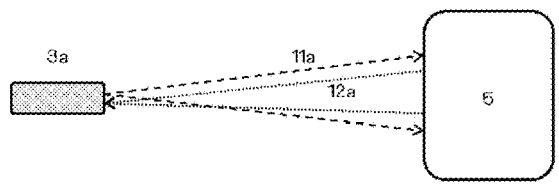

[Fig. 8]
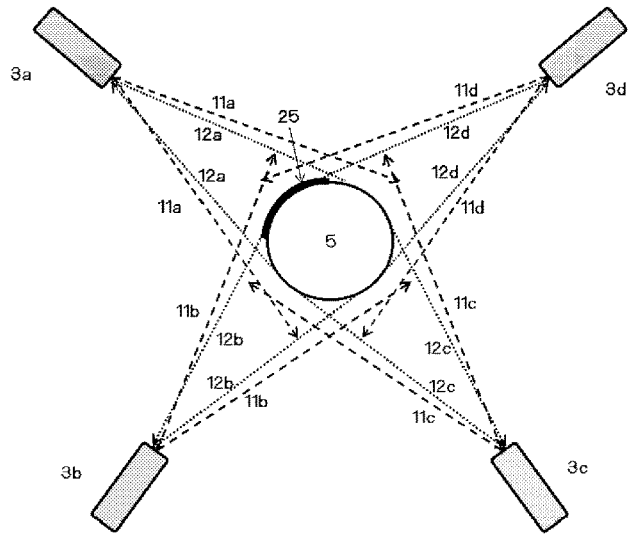
[Fig. 9]
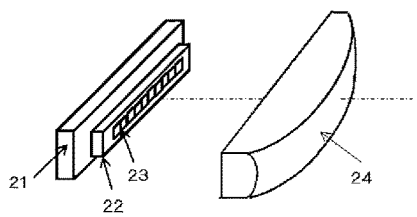
[Fig. 10]
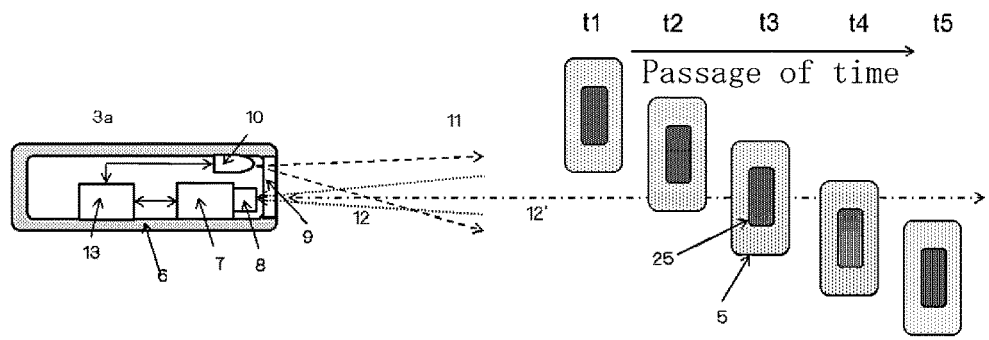
[Fig. 11]
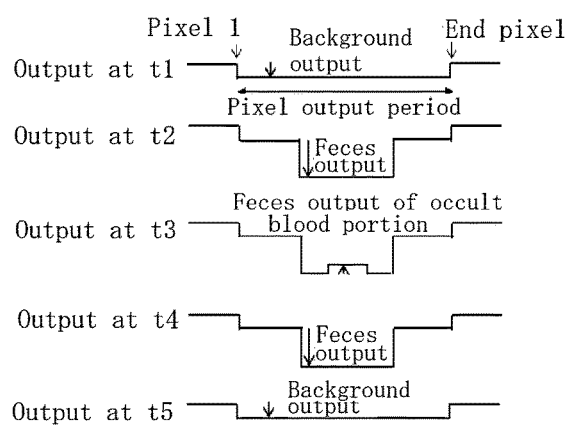

[Fig. 12(a)]
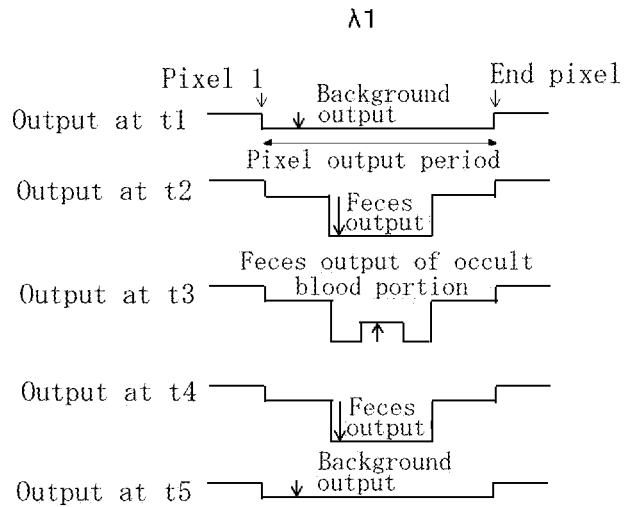
[Fig. 12(b)]
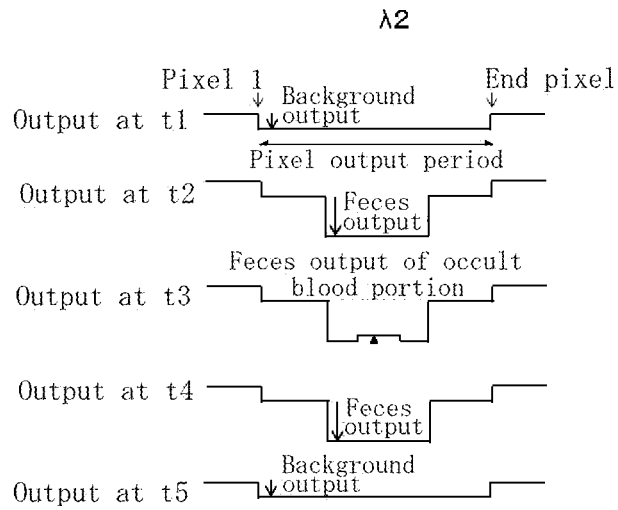
[Fig. 12(c)]
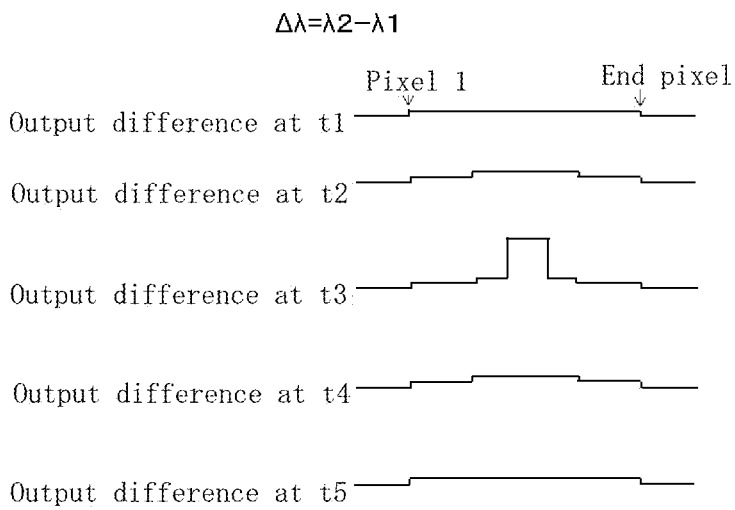

[Fig. 13(a)]
Output of sensing section 3(a)
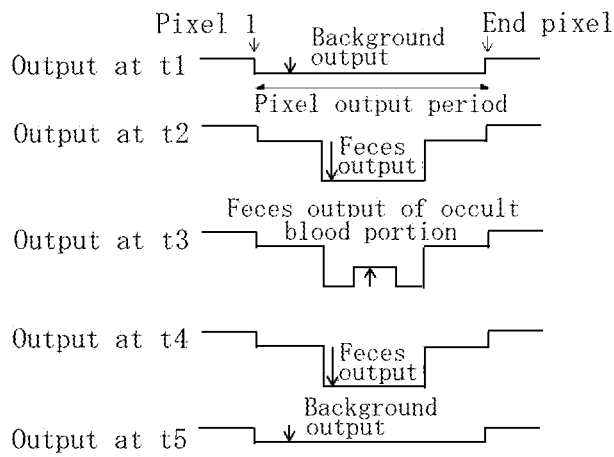
[Fig. 13(b)]
Output of sensing section 3(c)
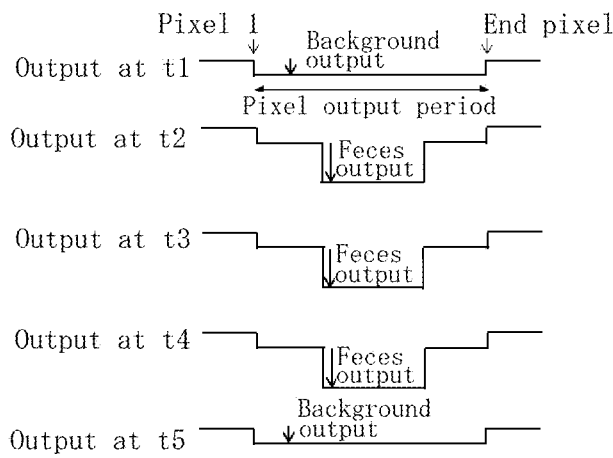
[Fig. 13(c)]
Output difference between sensing section 3(a) − sensing section 3(c)
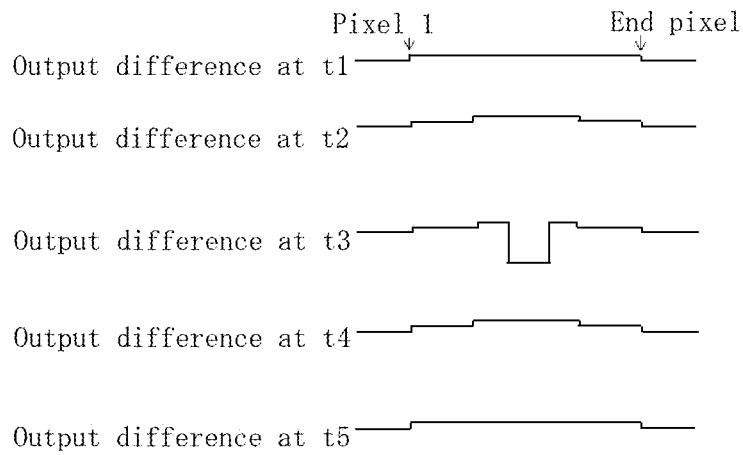

[Fig. 14(a)]
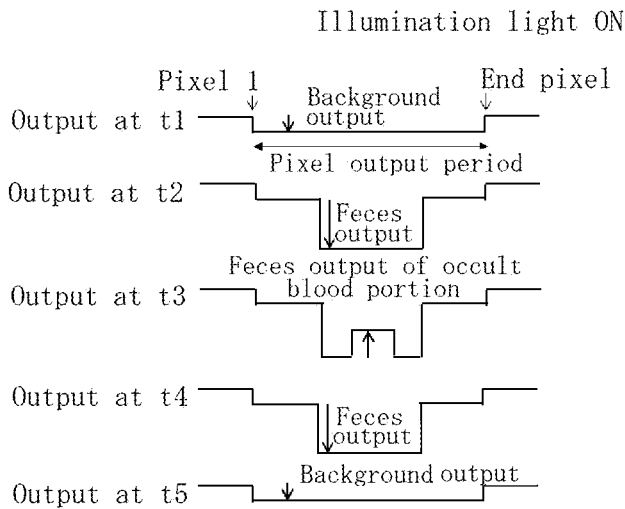
[Fig. 14(b)]
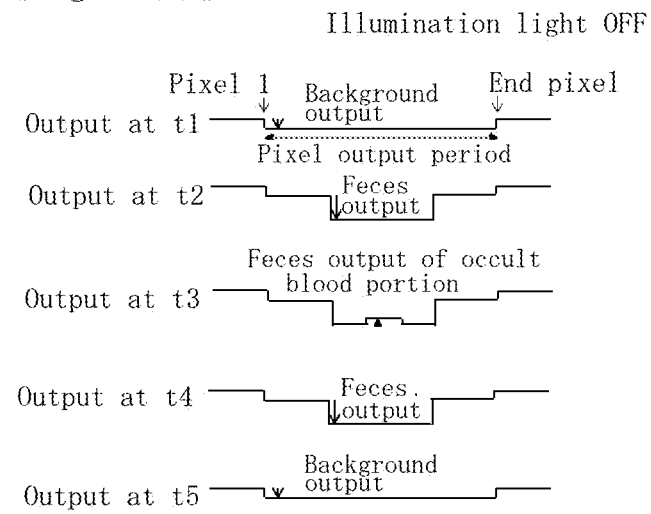
[Fig. 14(c)]
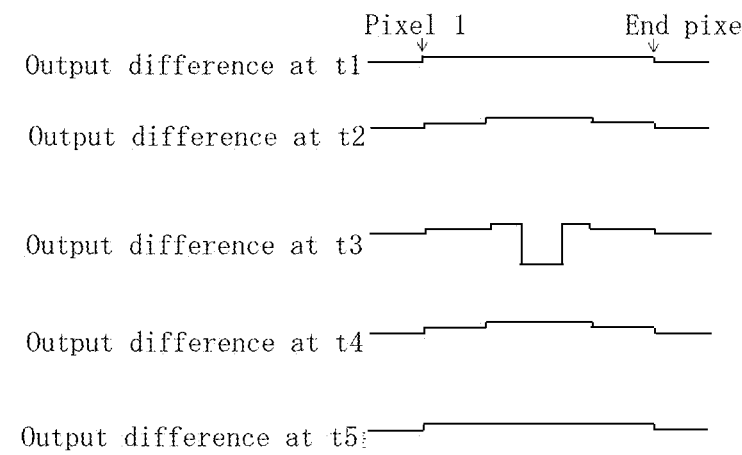

[Fig. 15]
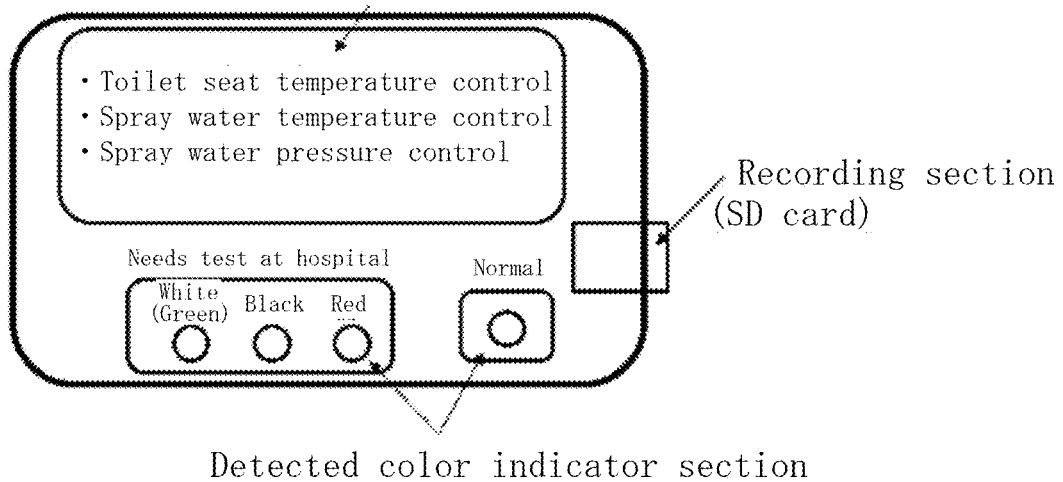

FECES COLOR DETECTION DEVICE

PRIORITY CLAIM

This application is a divisional of U.S. application Ser. No. 16/572,990, filed Sep. 17, 2019, which is a continuation of U.S. application Ser. No. 15/319,473, filed Dec. 16, 2016, which is a national phase of International Application No. PCT/JP2015/066420, filed Jun. 7, 2015, which claims priority to Japanese Application No. 2014-125844, filed Jun. 18, 2014, the contents of which are herein incorporated by reference in their entirety.

TECHNICAL FIELD

The present invention relates to a device for detecting the color of feces in the everyday life environment, monitoring the daily health state. Particularly, the present invention relates to a device for automatically detecting occult blood on the feces surface.

BACKGROUND ART

Detecting occult blood in feces is effective at finding colorectal diseases such as colorectal cancer. Fecal occult blood detection has been employed as a test in a regular medical checkup or a thorough medical examination and conducted in many public institutions and medical institutions for early detection and treatment of colorectal cancer and gastrointestinal diseases. Methods for testing fecal occult blood include chemical methods such as the benzidine method, the orthotolidine method and the guaiac method, the latex agglutination method using latex particles sensitized for an antibody and the chromatography method using a pigment bound on an antibody.

With these fecal occult blood test methods, the user lays sheets of paper such as toilet paper in the toilet bowl of a flush toilet to thereafter defecate onto the toilet paper, and the user scrapes the defecated feces with the fecal sampling pick of the container.

With a western-style toilet, however, feces easily sink into the water-seal portion of the toilet bowl to be mixed with urine, making it difficult to sample feces in the toilet bowl, and the hand may touch the feces when trying to sample the feces with the fecal sampling pick, which is unpleasant and unsanitary.

Moreover, another problem with this method is that it is only possible to detect an occult blood reaction from positions where the fecal sampling pick scraped, failing to detect occult blood in other portions, resulting in a low 50% detection rate for early-stage colorectal cancer. Also with the low testing frequency, i.e., thorough medical examinations and regular medical checkups, the death rate for colorectal cancer has now risen to the third highest for men and the highest for women, and is still on the rise. Under such circumstances, there is an increasing demand for the development of an examination technique that can be used in everyday life with a high accuracy.

Methods of conducting a fecal occult blood test in a bathroom in a hygienic manner without burdening the user include those of Patent Document No. 1 and Patent Document No. 2, in which feces excreted from a body are collected before the feces sink into the water-seal portion and the collected feces are dissolved in a solution, and the solution is transferred to detect the occult blood in the feces-dissolved solution by an immunoassay. However, these methods have problems such as the bad odor when collecting the feces, cleaning of the collecting device, and the complexity in the maintenance of the detection section.

Another method of conducting a fecal occult blood test in a bathroom is a method in which the defecation gas discharged from the human body during defecation is sucked in and the amine gas contained in the sucked defecation gas is detected with an amine sensor to detect an occult blood reaction based on the fact that the amount of amine gas increases when there is an occult blood reaction, as in Patent Document No. 3. With this method, the detection accuracy is not high when no defecation gas is discharged during defecation, and it is necessary to have a defecation gas suction part in the vicinity of the feces and it is also necessary to clean the tip of the suction part.

On the other hand, Patent Document No. 4 discloses an excrement checking device for capturing the image of an excrement in the toilet bowl and displaying the image so that the user can view the image while in a seated position. It captures the image of the inside of the toilet bowl with a camera, and the user can observe the shape and the color of feces in a seated position by looking at the monitor screen. This method merely allows the user to look at the feces in a seated position and is not different from looking directly at the feces with naked eyes, and there is a problem in that the user feels reluctant to observe with naked eyes every time.

As a method for monitoring the blood, pulse oximeters are well known in the art that examine the degree of oxygen saturation in the blood. This is a method of examining the blood oxygen concentration by using the transmission intensities of near infrared emissions of different wavelengths through blood vessels at a finger tip, based on the difference in absorption spectrum between oxygenated hemoglobin and deoxygenated hemoglobin. FIG. 1 shows typical absorption coefficient spectra. The vertical axis represents the absorption coefficient, and oxygenated hemoglobin has no absorption at 670 nm and therefore the transmitted light appears red. Deoxygenated hemoglobin has increased absorption, thereby appearing blackish. A pulse oximeter is a method of examining the blood oxygen concentration based on transmitted light.

CITATION LIST

Patent Literature

Patent Document No. 1: Japanese Laid-Open Patent Publication No. H10-31016
Patent Document No. 2: Japanese Laid-Open Patent Publication No. H10-260182
Patent Document No. 3: Japanese Laid-Open Patent Publication No. 2006-132948
Patent Document No. 4: Japanese Laid-Open Patent Publication No. 2006-61296

SUMMARY OF INVENTION

Technical Problem

With the occult blood test method using a fecal sampling pick, which is commonly conducted in regular medical checkups and thorough medical examinations, the test frequency is as low as one or twice a year. Moreover, if the sampling area to be sampled with the fecal sampling pick is small, the occult blood portion may not be found, resulting in a low detection rate for early-stage colorectal cancer. The method of sampling the feces with a fecal sampling pick also has a problem of being unsanitary.

Methods in which the detection is performed during defecation in a household toilet bowl have a problem in that the detection is done only rarely due to the high maintenance cost of the test, as well as other problems: the feces are sampled or the defecation gas is sampled during defecation, not only making is necessary to clean the sampling area, but also complicating the maintenance of the sensor and making it necessary to provide a means for preventing cross contamination with the subject immediately before the test.

The color of feces is sometimes visually observed at home, but it is a sensual determination, and it is not possible to observe changes over days. With the fecal occult blood determination relating to colorectal cancer, one will not notice it until the disease advances to such a degree that it can be recognized with naked eyes, and one may possibly overlook early-stage cancer. Beside the occult blood determination, there is a problem in that when the color of feces changes gradually, one may not notice the change until the disease reaches an advanced stage.

Solution to Problem

According to an embodiment of the present invention, a plurality of color cameras are provided on the reverse side portion of the toilet seat so as to capture an image of the feces surface from a plurality of directions and observe the color of the feces surface. The data of the feces color is recorded as time-series data to quantitatively grasp changes in feces color. Particularly, the presence/absence of occult blood, which is highly correlated to colorectal cancer, is determined on a daily basis. The detection accuracy is improved by comparison with other wavelength ranges based on the wavelength spectrum distribution of oxygenated hemoglobin corresponding to an occult blood reaction.

Advantageous Effects of Invention

With a feces color detection device of the present invention, it is possible to easily observe changes in the color of the feces surface upon defecation on a daily basis, and to detect changes in the color of the feces surface, which is correlated to health, particularly, occult blood, in a hygienic manner. With this method of optically detecting occult blood on the feces surface, cameras are provided on the reverse side of the toilet seat, thereby enabling detection at locations away from the position of defecation, only requiring simple maintenance of processing signals of images captured by the cameras and requiring no special reagents, thus facilitating daily monitoring. It also enables the feces surface observation from a plurality of directions, making it unlikely to overlook an occult blood reaction on the surface. An advantage is that a test can be conducted without the user being aware of it during defecation on a daily basis, leading to early detection of colorectal cancer and thus decreasing the death rate.

By using a linear sensor including three color filters of red, blue and green as the image sensor in each color camera, it is possible to alleviate the feeling of reluctance of being captured by cameras during defecation. This is due to the fact that although a linear sensor can only capture an image of a stationary object on the same line each time, thus failing to grasp the entire image, it can capture the surface conditions of a moving object.

BRIEF DESCRIPTION OF THE DRAWINGS

FIG. 1 shows absorption coefficient spectra of oxygenated hemoglobin and deoxygenated hemoglobin in blood.

FIG. 2 is a side view of a toilet showing how the feces surface is observed during defecation according to the first embodiment of the present invention.

FIG. 3(a) is a bottom view of a toilet seat according to the first embodiment of the present invention, FIG. 3(b) is a front view of the toilet seat, and FIG. 3(c) is a front view of a toilet bowl, and FIG. 3(d) is a side view of the toilet seat.

FIG. 4 is a structure diagram of a color sensing section including an image-capturing camera, showing a light-output area for outputting illumination light and a light-input area for receiving image-capturing light, according to the first embodiment of the present invention.

FIG. 5 is a view illustrating a lighting illuminator and a light-output area for outputting illumination light according to the first embodiment of the present invention.

FIG. 6 is a structure diagram of an image-capturing camera in which an area sensor is used as the image-capturing element according to the first embodiment of the present invention.

FIG. 7 is a view showing an optical relationship between a single color sensing section of FIG. 4 and FIG. 6 and feces as the subject, as seen from the side direction, according to the first embodiment of the present invention.

FIG. 8 is a view showing an optical relationship between a plurality of color sensing sections and feces as the subject, as seen from the toilet seat bottom surface direction, according to the first embodiment of the present invention.

FIG. 9 is a structure diagram of an image-capturing camera in which a linear sensor and a cylindrical lens are used as the image-capturing element according to the second embodiment of the present invention.

FIG. 10 is a structure diagram of a color sensing section including an image-capturing camera, showing the relative positions over time between the light-output area for outputting illumination light, the line of image-capturing light to be received by pixels of the linear sensor, and feces as the subject, according to the second embodiment of the present invention.

FIG. 11 is a diagram showing output waveforms over time of the linear sensor according to the second embodiment of the present invention.

FIG. 12(a) is a diagram showing conceptual output waveforms over time of the linear sensor when the illumination wavelength is in a wavelength range (λ1) where the absorptance in blood is high, according to the third embodiment of the present invention.

FIG. 12(b) is a diagram showing conceptual output waveforms over time of the linear sensor when the illumination wavelength is in a wavelength range (λ2) where the absorptance in blood is low, according to the third embodiment of the present invention.

FIG. 12(c) is a diagram showing conceptual differential output waveforms over time of the linear sensor between when the illumination wavelength is in one of two wavelength ranges (λ1 and λ2) and when the illumination wavelength is in the other wavelength range, according to the third embodiment of the present invention.

FIG. 13(a) is a diagram showing conceptual output waveforms over time of the linear sensor of the sensing section 3(a) in the layout shown in FIG. 8 when the illumination wavelength is in the wavelength range (λ1) where the absorptance in blood is high, according to the fourth embodiment of the present invention.

FIG. 13(b) is a diagram showing conceptual output waveforms over time of the linear sensor of the sensing section 3(b) in the layout shown in FIG. 8 when the illumination wavelength is λ1, according to the fourth embodiment of the present invention.

FIG. 13(c) is a diagram showing conceptual differential output waveforms over time between the linear sensors of the sensing section 3(a) and the sensing section 3(b) in the layout shown in FIG. 8 when the illumination wavelength is λ1, according to the fourth embodiment of the present invention.

FIG. 14(a) is a diagram showing conceptual output waveforms over time of the linear sensor when the illumination light is turned ON, according to the fifth embodiment of the present invention.

FIG. 14(b) is a diagram showing conceptual output waveforms over time of the linear sensor when the illumination light is turned OFF, according to the fifth embodiment of the present invention.

FIG. 14(c) is a diagram showing conceptual differential output waveforms over time of the linear sensor between when the illumination light is turned ON and when the illumination light is turned OFF, according to the fifth embodiment of the present invention.

FIG. 15 is a view showing a color indicator section according to the seventh embodiment of the present invention.

DESCRIPTION OF EMBODIMENTS

A method for arranging cameras at positions along the toilet seat according to an embodiment of the present invention, and a method for detecting occult blood of a feces surface portion based on the arrangement will now be described with reference to the drawings. In the following description, like parts will be denoted by like reference signs and like process names, and they will be described in detail at first, thereafter omitting redundant description of like parts.

Embodiment 1

FIG. 2 and FIG. 3 are views illustrating the first embodiment of the present invention, but the concept also applies to other embodiments.

In FIG. 2, 1 denotes a toilet bowl, with a toilet seat 2 provided thereon. A plurality of color sensing sections 3a and 3b are provided on the reverse side of the toilet seat. The structure is such that before feces 5 excreted from a body 4 sink into a water-seal portion (not shown) of the toilet bowl 1, the surface of the feces 5 is observed from a plurality of directions by means of the color sensing sections 3a and 3b.

In the figures, broken line portions of the toilet seat 2 correspond to the end position of the opening of the toilet seat on the inner side thereof.

The structure of the toilet seat 2 will be described in greater detail with reference to FIG. 3. FIG. 3(a) shows the configuration of the reverse side (the toilet bowl side) of the toilet seat 2. A plurality of color sensing sections 3a, 3b, 3c and 3d are arranged on the reverse side of the toilet seat 2. Normally, in order to keep the toilet seat 2 clean, a plurality of spacer portions are provided on the reverse side portion of the toilet seat 2 to give a spacing between the upper portion of the toilet bowl 1 and the toilet seat 2. In FIG. 2 and FIG. 3, the color sensing sections 3a, 3b, 3c and 3d also serve as the spacer portions.

FIG. 3(b) is a front view of the toilet seat 2, and the color sensing sections 3a, 3b, 3c and 3d, to serve as spacers, are provided on the reverse side of the toilet seat 2. FIG. 3(c) is a front view of the toilet bowl 1. The toilet seat 2 is arranged in contact with an upper peripheral portion 1' of the toilet bowl 1 with the color sensing sections 3a, 3b, 3c and 3d therebetween. FIG. 3(d) is a side view of the toilet seat 2.

In the figure, the broken line portions of the toilet seat 2 and the toilet bowl 1 correspond to the end portion of the opening of the toilet seat and the toilet bowl on the inner side thereof.

The structure of the color sensing section 3a of the toilet seat 2 will be described with reference to FIG. 4. The structure is also the same for the other color sensing sections 3b, 3c and 3d. The color sensing section 3a includes, provided inside a housing 6, an image-capturing system and an illumination system, wherein the image-capturing system includes an image-capturing camera 7, a lens portion 8 of the image-capturing camera and an optical window 9, and the illumination system includes an illumination section 10 for outputting illumination light. A light-output area 11 for illumination light output from the illumination section 10 is denoted by a broken line in FIG. 4, and a light-input area 12 for receiving image-capturing light from the subject is denoted by a dotted line in FIG. 4. A control section 13 is provided in the housing 6, thereby synchronizing the illumination section 10 and the image-capturing camera 7 with each other to obtain a captured image corresponding to the illumination light.

The illumination section 10 in FIG. 4 may use a white LED, the image-capturing camera 7 may use a Bayer-type color camera including an arrangement of color filters of the three primary colors (red, blue and green), a color camera of such an arrangement that an infrared light filter is provided in a portion of the color filter, or a filter configuration in which a portion of the color filter is transparent light.

Ambient light coming from the gap under the toilet seat may be used, while omitting the white LED.

The image-capturing camera may use a black-and-white camera with no color filter, and LED illumination sections of three colors (red, blue and green) may be successively illuminated to capture images in a time division manner.

As for the detection of the color of feces, the color of feces can be easily determined using conventional techniques by calculating signal levels for the three colors (red, blue and green) based on the captured signals of the three colors, and comparing them with respect to the reference signal level (range) of the color to be determined, as with ordinary color cameras.

The control section 13 of FIG. 4 is capable not only of controlling the illumination system and the image-capturing system of the single color sensing section 3a, but also of performing a control in cooperation with the illumination systems and the image-capturing systems of the color sensing sections 3b, 3c and 3d.

The structure of the illumination section 10 of FIG. 4 will be described with reference to FIG. 5. The illumination section 10 includes illuminators 15a and 15b provided on a circuit board 14, and a lens-shaped transparent resin 16 is used to align the output direction of the illumination light output from the illuminator (15a in the figure). Thus, it is possible to narrow the width of the light-output area 11 for outputting illumination light and to increase the intensity of the illumination light.

When LEDs are used as the illuminators 15a and 15b in the illumination section 10 of FIG. 5, the size of the illuminator is sufficiently smaller than the size of the lens-shaped transparent resin 16. Therefore, by arranging the illuminators 15a and 15b in the vicinity of each other, the light-output areas 11 for the individual illuminators can be substantially aligned with each other. Herein, by varying the emission wavelength between the illuminators 15a and 15b, it is possible to obtain the output from each pixel with respect to illumination light of different wavelength ranges.

The structure of the image-capturing camera 7 of FIG. 4 will be described with reference to FIG. 6. In FIG. 6, an area sensor 18 is provided, as the image-capturing element, on a circuit board (not shown) of an image-capturing camera housing 17, and the area sensor 18 corresponds to the lens portion 8 of FIG. 4, with a lens 19 arranged in a lens barrel 20. The image of the subject on the lens 19 forms an image on pixels (not shown) of the area sensor. The use of the area sensor 18 as the image-capturing element is a characteristic of the image-capturing camera of Embodiment 1.

FIG. 7 is a view showing an optical relationship between the single color sensing section 3a of FIG. 4 and FIG. 6 and the feces 5 as the subject, as seen from the side direction, according to the first embodiment of the present invention. A light-output area 11a for illumination light, denoted by a broken line, output from the color sensing section 3a of the toilet seat 2 is reflected on the surface of the feces 5 as the subject to be received by the color sensing section 3a as a light-input area 12a denoted by a dotted line. Inside the color sensing section 3a, the image of the subject received via the optical window forms an image on pixels of the area sensor via the lens portion.

FIG. 8 is a view showing an optical relationship between the color sensing sections 3a, 3b, 3c and 3d of FIG. 3 and the feces 5 as the subject, as seen from the toilet seat bottom surface direction, according to the first embodiment of the present invention. The light-output area 11a for illumination light, denoted by a broken line, output from the color sensing section 3a of the toilet seat 2 is reflected on the surface of the feces 5 as the subject to be received by the color sensing section 3a as the light-input area 12a denoted by a dotted line. This similarly applies to the other color sensing sections 3b, 3c and 3d, with their light-output areas denoted as 11b, 11c and 11d and their light-input areas as 12b, 12c and 12d.

As shown in FIG. 8, with the light-output areas for outputting illumination light, denoted as 11a, 11b, 11c and 11d, the entire circumference of the feces 5 as the subject is illuminated. The light-input areas 12a, 12b, 12c and 12d for receiving, into the color sensing section, the reflected light from the feces 5, denoted by dotted lines, capture the entire circumference of the feces 5 as the subject with overlap with one another.

In FIG. 8, an occult blood area 25 is partially present on the surface of the feces 5. With such an optical system, the occult blood portion 25 can be detected in edge portions of the images from the image-capturing cameras of the color sensing sections 3b and 3d, as well as by the image-capturing camera of the color sensing section 3a. Since the image-capturing camera is capable of color image-capturing, such an optical system can determine the presence/absence of blood based on the color information of the occult blood area 25 of the feces surface.

In FIG. 5, by varying the wavelength between the illuminators 15a and 15b, it is possible to improve the accuracy in sensing the occult blood area 25 on the surface of the feces 5. That is, the occult blood area can be irradiated with illumination light of a wavelength range of red and illumination light of a wavelength range of the complementary color of red (cyan), and it is possible to grasp the characteristic of the color of the occult blood area based on the output values of pixels corresponding to the respective color filters.

Embodiment 2

As the second embodiment of the present invention, a structure in which a linear sensor is used as the image-capturing element of the image-capturing camera 7 of the color sensing section will be described with reference to FIG. 9. In FIG. 9, a linear sensor 22 is provided, as the image-capturing element, on a circuit board 21, and with pixels 23 on the linear sensor in a linear arrangement, it is possible to obtain linear images. For the lens of the linear sensor, a cylindrical lens 24 is used as the component, of which the lens size in the vertical direction and that in the horizontal direction are significantly different from each other as shown in FIG. 9.

FIG. 10 shows a diagram showing the structure of the color sensing section 3a of the toilet seat 2 and the structure of the color sensing section including the image-capturing camera according to the second embodiment of the present invention. FIG. 10 is similar to FIG. 4 and FIG. 7 of Embodiment 1, and the light-output area 11 for illumination light output from the illumination section 10 is the same, but FIG. 10 is characteristic in that the input light to be input on the pixels in a linear arrangement, of the light-input area 12 from the feces 5 as the subject to be received by the pixels of the linear sensor, does not have a width and is in a linear shape, as opposed to Embodiment 1. The light-input area 12 is denoted as a light-input area line 12' in FIG. 10 and denoted by a one-dot-chain line so as to be distinguished from FIG. 7 of Embodiment 1.

FIG. 10 illustrates an optical system of the color sensing section 3a capable of detecting the occult blood portion 25 of the feces 5 as the subject. In the figure, the elapse of time during the downward movement of the feces 5 is represented by times t1, t2, t3, t4 and t5. While the light-input area line 12' which can be captured by the pixels of the linear sensor is denoted by a one-dot-chain line, the occult blood portion 25 of the feces 5 is captured by the linear sensor at time t3. The feces 5 as the subject are not captured at times t1 and t5, and a part of the feces 5 as the subject where the occult blood portion 25 is absent is captured at times t2 and t4.

The illumination light output from the illumination section 10 and the image-capturing camera 7 for capturing an image of the subject are synchronized with each other by means of the control section 13 in the housing 6, as in FIG. 7, thereby making it similarly possible to obtain a captured image corresponding to the illumination light.

FIG. 11 shows output waveforms of the linear sensor at times t1, t2, t3, t4 and t5 of FIG. 10. At times t1 and t5, when an image of the feces of the subject is not being captured, a background output is output. In the figures, the opposite ends of the pixel output period are represented by the first pixel output (Pixel 1) and the last pixel output (end pixel), respectively.

In FIG. 11, at times t2 and t4, when an image of the feces 5 of the subject in an area where the occult blood portion 25 is absent, the illumination light output from the illumination section 10 is reflected by the surface of the feces 5 of the subject, which is present at a shorter distance than the background, to return to the sensing section. Therefore, as the output waveform, this reflected light component from the feces surface ("feces output" in the figures) appears, in addition to the background output, on the light-input area line 12'. The feces output is determined by the reflectivity of the illumination light at the feces surface and the intensity of the illumination light at the feces surface portion.

In FIG. 11, at time t3, when an image of the occult blood portion 25 of the feces 5 is captured, the illumination light output from the illumination section 10 passes through the occult blood portion 25 adhering to the surface of the feces 5 and is reflected by the feces surface to again pass through the occult blood portion 25 and return to the sensing section. Therefore, as the output waveform, this feces output of the occult blood portion appears, in addition to the background output and the feces output, on the light-input area line 12'. The feces output of the occult blood portion is determined by the absorption coefficient of the illumination light at the occult blood portion, the reflectivity of the illumination light at the feces surface, and the intensity of the illumination light at the feces surface portion. Herein, the absorption coefficient of the illumination light at the occult blood portion varies depending on the proportion of oxygenated hemoglobin in the occult blood portion and the wavelength of the illumination light, as shown in FIG. 1.

Embodiment 3

As the third embodiment of the present invention, where a linear sensor is used as the image-capturing element of the image-capturing camera 7 of the color sensing section, FIGS. 12(*a*) and 12(*b*) show output waveforms of a linear sensor at times t1, t2, t3, t4 and t5 of FIG. 10 when the wavelength of the illumination light is varied.

Herein, sensing in which the wavelength of the illumination light is varied in the infrared light region, which is not a visible range, is also referred to as color sensing.

FIG. 12(*a*) shows output waveforms of the linear sensor at times t1, t2, t3, t4 and t5 of FIG. 10, when the wavelength of the illumination light is $\lambda 1$. The wavelength $\lambda 1$ of FIG. 12(*a*) corresponds to a wavelength range where the absorption coefficient of the occult blood portion is large, and corresponds to a visible range of 600 nm or less or a near infrared region wavelength range of 800 nm or more in FIG. 1.

FIG. 12(*b*) shows output waveforms of the linear sensor at times t1, t2, t3, t4 and t5 of FIG. 10, when the wavelength of the illumination light is $\lambda 2$. The wavelength $\lambda 2$ of FIG. 12(*b*) corresponds to a wavelength range where the absorption coefficient of the occult blood portion is small, and corresponds to a wavelength range of around 670 nm in FIG. 1.

FIG. 12(*c*) shows output waveforms obtained as the difference between the output waveforms of the linear sensor at times t1, t2, t3, t4 and t5 of FIG. 10 when the wavelength of the illumination light is $\lambda 2$ and those when the wavelength of the illumination light is $\lambda 1$. It is possible to increase the detection accuracy by extracting the signal of the occult blood portion utilizing the difference depending on the wavelength of the absorption coefficient of the occult blood portion. The signal level difference in the absence of occult blood (deoxygenated hemoglobin increases the absorption, appearing blackish) is adjusted beforehand, including the difference in the sensitivity of the image-capturing element to the wavelengths $\lambda 2$ and $\lambda 1$, and the difference in the light intensity due to the difference in the wavelength of the illumination light. Normally, the adjustment is done in advance before shipping the product. Then, when an image of the feces with occult blood is captured, it is possible to accurately extract only the signal of the occult blood portion as shown in FIG. 12(*c*).

As shown in FIG. 1, the absorptance of oxygenated hemoglobin rapidly increases on the short wavelength side and on the long wavelength side, with the absorptance minimized in a wavelength range of around 670 nm. It is important to observe this portion for the fecal occult blood reaction.

The absorption spectrum of blood is determined by hemoglobin of red blood, which accounts for about a half the volume of blood, as shown in FIG. 1. There are two types of hemoglobin in blood, i.e., oxygenated hemoglobin and deoxygenated hemoglobin, and the reflection spectrum varies depending on the amount of oxygen bound to hemoglobin. The graph is characteristic in that oxygenated hemoglobin has a local minimum point of absorption at 670 nm.

The typical blood oxygen saturation is 95% to 98% in the arteries and 60% to 80% in the veins. Therefore, when occult blood is adhering to the feces surface, if the adherent blood is arterial blood, light is reflected by the feces surface without being substantially absorbed in the wavelength range of 670 nm, thus appearing red. Therefore, it is important to make a comparison between 670 nm and other wavelength ranges.

Also when the adherent blood is venous blood, the main component thereof is oxygenated hemoglobin, and there is a tendency that the absorptance is locally minimized at 670 nm, but the tendency is not as significant as that with arterial blood. Oxygenated hemoglobin and deoxygenated hemoglobin both have a significant difference in absorptance between a wavelength range of 600 nm or less and a 670 nm wavelength range. As shown in FIG. 1, it is preferred that the wavelength of the illumination light is in a range from 600 nm to 800 nm, where there is a significant hemoglobin difference, and is particularly a single wavelength around 670 nm, where the half-value width is narrow (20 nm to 140 nm). Using a wavelength of 670 nm, there is an about 10 times sensitivity difference, and when deoxygenated hemoglobin is contained, the light absorption coefficient is large, resulting in a low sensor output signal level. On the other hand, when no deoxygenated hemoglobin is contained, the light absorption coefficient is small, resulting in a high sensor output signal level. It is possible to determine the presence/absence of occult blood from the sensor output signal level, and it is possible to effectively give a warning of colorectal cancer and gastrointestinal diseases.

Embodiment 4

As the fourth embodiment of the present invention, where a linear sensor is used as the image-capturing element of the image-capturing camera 7 of the color sensing section, FIGS. 13(*a*) and 13(*b*) show output waveforms of the linear sensor at times t1, t2, t3, t4 and t5 of FIG. 10, when the sensing section position is varied (the sensing sections 3(*a*) and 3(*c*) of FIG. 8) in the sensing section layout of FIG. 8.

FIG. 13(*a*) shows output waveforms of the linear sensor of the sensing section 3(*a*) at times t1, t2, t3, t4 and t5 of FIG. 10, when the wavelength of the illumination light is $\lambda 1$. The wavelength $\lambda 1$ of FIG. 13(*a*) corresponds to a wavelength range where the absorption coefficient of the occult blood portion is large, and corresponds to a wavelength range in a visible range of 600 nm or less in FIG. 1.

FIG. 13(*b*) shows output waveforms of the linear sensor of the sensing section 3(*c*) at times t1, t2, t3, t4 and t5 of FIG. 10, also when the wavelength of the illumination light is $\lambda 1$. The occult blood portion 25 cannot be detected by the sensing section 3(*c*), which does not give the feces output of the occult blood portion at time t3.

FIG. 13(*c*) shows output waveforms obtained as the difference between the output waveforms of the linear sensor of the sensing section 3(*a*) and those of the linear sensor of the sensing section 3(c) at times t1, t2, t3, t4 and t5 of FIG. 10, also when the wavelength of the illumination light is 1. It is possible to increase the accuracy in detecting the occult blood portion utilizing the difference depending on the presence/absence of the occult blood portion.

Embodiment 5

As the fifth embodiment of the present invention, where a linear sensor is used as the image-capturing element of the image-capturing camera 7 of the color sensing section, FIG. 14(a) shows output waveforms of the linear sensor at times t1, t2, t3, t4 and t5 of FIG. 10, when illumination light of the sensing section having a wavelength of λ1 is emitted (ON) in the sensing section (FIG. 3(a)) layout of FIG. 8. In this case, illumination due to ambient light is superposed, in addition to the illumination light from the sensing section, deteriorating the accuracy in giving the feces output of the occult blood portion.

FIG. 14(b) shows output waveforms of the linear sensor at times t1, t2, t3, t4 and t5 of FIG. 10, when the illumination light of the sensing section is not emitted (OFF). Since the illumination light is not emitted, there is only illumination from ambient light, resulting in a weak lighting intensity and a low output. Since there is only illumination from ambient light, the wavelength has a broad wavelength band, resulting in a poor accuracy in giving the feces output of the occult blood portion.

FIG. 14(c) shows differential output waveforms of the linear sensor at times t1, t2, t3, t4 and t5 of FIG. 10 between when the illumination light of the sensing section is emitted (ON) and when it is not emitted (OFF). By obtaining the difference from the output when the illumination light is not emitted, i.e., when there is only illumination from ambient light, it is possible to cancel out. This improves the accuracy in giving the feces output of the occult blood portion.

Embodiment 6

As the sixth embodiment of the present invention, it is possible to increase the occult blood detection accuracy based on the frequency distribution of the location where the occult blood portion is detected, by recording output waveforms from a plurality of color sensing sections 3a, 3b, 3c and 3d shown in FIG. 8 every time, and not determining occult blood portion information only from one time but checking it against the recorded history of the same person. This is based on the fact that a person normally sits in the same direction during defecation and the fact that the feces are unlikely to rotate during the feces peristaltic movement through the large intestine, so that once an occult blood reaction starts to be observed, the fecal occult blood portion is repeatedly located in the same direction.

In the sixth embodiment of the present invention, a toilet bowl/toilet seat used by a plurality of persons needs to identify the same person. For this, it is possible to identify the person based on the body weight by adding a pressure sensor (not shown) to the color sensing sections 3(a), 3(b), 3(c) and 3(d), as well as by using an input (not shown) made by the person for each use. Data of deviation between the plurality of pressure sensors can also be used for identifying the person, and the color of feces can be used for identifying the person.

In the first to sixth embodiments of the present invention, it is necessary not only to identify the same person but also to record and read data for the same person at a point in time after the color sensing section. For this, a recording means (not shown) may be provided in the control section to store data therein, or a communication means (not shown) may be provided in the control section to send data to a main server or a portable information terminal so that the data is recorded/stored in the main server or the portable information terminal.

Embodiment 7

As the seventh embodiment of the present invention, FIG. 15 shows an indicator section for indicating the color determined by the feces color detection device. This indicator section is built in the control section of the washing device. As for the connection with the color sensing section, detected color information is transmitted via wire or radio. The washing device section includes a section for controlling the temperature of the toilet seat, a section for controlling the temperature of the spray water, and a section for controlling the pressure of the spray water. The color determined by the feces color detection device can be indicated by lighting LED lamps. This includes an LED that indicates "normal", and other LEDs for indicating typical colors (e.g., white (green), black, red). On the color indicator sections for these three colors, there is a label prompting the user to take a test at a hospital. It further includes a memory (e.g., an SD card) section for recording detected color information. This recorded data may also record the signal levels for red, blue and green so that the levels of these colors can be displayed on a personal computer. This data can be submitted to a hospital to improve the test accuracy by taking time-series data into consideration.

Embodiment 8

Embodiments of the present invention have been described above while focusing on the presence/absence of an occult blood portion on the feces surface to assist in early detection of colorectal cancer. However, the method for observing the color of the feces surface according to the present invention can be used not only to simply determine the occult blood portion, but also to follow changes in the color of the feces surface for the general health care of the person.

That is, it is believed that the color of feces contains information of the digestive system, and not only the red coloring due to colorectal cancer, for example, but also gastric ulcer, duodenal ulcer, and abnormalities of the pancreas, the small intestine and the large intestine, etc., are correlated to the color of feces. Other than by obtaining data by capturing color images, it is possible to determine the health state by combining it with the LED emission wavelength of the illumination section, as in the spectral representation of an occult blood reaction.

A deep green color indicates the possibility of a bile stone stuck in the bile duct, jaundice, pancreatic cancer or liver cancer, a deep black coal tar color indicates the possibility of bleeding of the stomach, and a black color is the color of oxidized iron in blood, indicating the possibility of gastric ulcer, duodenal ulcer or gastric cancer. Blood is mixed in the feces, i.e., hemorrhagic feces, indicates the possibility of troubles of the large intestine, as well as colorectal cancer. Moreover, bright-red blood indicates the possibility of rectal cancer.

In any of these cases, the color indicator device indicates the color and prompts the user to take a test at a hospital so that the user will immediately take a formal test.

A normal color of feces is yellowish brown. Then, the color detection results may be recorded and continued observation may take place.

Embodiment 9

Embodiments of the present invention have been described above regarding a system in which a camera is started to continually capture the image after a pressure sensor detects a user sitting in place or after a test start switch is turned ON.

However, continually capturing the image increases the power consumption. In view of this, it is possible to detect the motion of feces by using the camera in a low power consumption mode by performing a binning or thinned image-capturing operation in which the number of output pixels is reduced to compare between image signals from different capture times. Then, immediately after a motion is detected, an image-capturing operation in the normal capturing mode is performed, and after the color is detected, the system is turned OFF, thus realizing a feces color detection device capable of an energy saving operation.

Embodiment 10

While individual embodiments of the present invention have been described above, it is understood that each embodiment can be used in combination with others rather than alone.

While the description above is directed to cases where the sensing sections are provided inside the spacer portions on the bottom surface of the toilet seat, the sensing sections may be provided other than in the spacer portions. As for the alternative locations to provide the sensing sections, the sensing sections may be provided on the upper edge portion of the toilet bowl or may be embedded in the upper portion of the toilet bowl.

When an excreting part washing device is built in the toilet seat according to the present invention shown in FIG. 2, it is possible to accurately detect the position of the feces through a three-dimensional image-capturing operation by using the plurality of sensing sections of FIG. 8. By controlling the washing direction toward which warm water is sprayed, based on the detected position, using a direction control device, it is possible to accurately aim at the position to be washed.

INDUSTRIAL APPLICABILITY

As described above, with the feces color detection device of the present invention, which observes the color of the feces surface every time the user defecates, it is possible to detect occult blood on the feces surface without the user being aware of it, as well as monitoring changes in the health state. Because it can be implemented with a simple structure without any extensive structure, it can be used for the purpose of general health care of a user himself/herself or for testing the health state, and may also be used as a toilet bowl (toilet seat) at a hospital or installed in a public bathroom, allowing a fecal occult blood reaction to be detected very inexpensively without using any reagent.

This enables early detection of colorectal cancer, which sits high in the cancer death rate rankings, thus saving the medical expense and elongating the average life span.

REFERENCE SIGNS LIST

1 Toilet bowl
2 Toilet seat
3 Color sensing section
4 Body
5 Feces
6 Sensing section housing
7 Image-capturing camera
8 Lens portion
9 Optical window
10 Illumination section
11 Light-output area
12 Light-input area
12' Light-input area line
13 Control section
14 Circuit board for illuminator
15 Illuminator
16 Lens-shaped transparent resin
17 Image-capturing camera housing
18 Area sensor
19 Lens
20 Lens barrel
21 Circuit board for linear sensor
22 Linear sensor
23 Linear sensor pixel
24 Cylindrical lens
25 Occult blood portion

The invention claimed is:

1. A toilet seat comprising:
at least one housing having an illumination section and a linear sensor configured to obtain a plurality of linear images, each of said plurality of linear images having a height of exactly one pixel and a width of a plurality of pixels; and
a control section being within the at least one housing;
wherein the toilet seat is configured to being provided on a toilet bowl,
the illumination section includes illuminators substantially aligned with one another and further includes a first lens,
the illuminators are configured to output illumination light to feces through the first lens before the feces sink into a water-seal portion of the toilet bowl,
the illuminators emit at least two different emission wavelengths,
the linear sensor has light-receiving pixels arranged in a linear array and a second lens in front thereof, and is configured to receive reflected light generated by reflection of the illumination light at the feces through the second lens,
the control section is operatively connected to the illumination section and the linear sensor, and configured to actuate the illuminators in order to successively illuminate the at least two different emission wavelengths in a time division manner and coincidentally actuate the linear sensor to obtain reflected light components reflected from a surface of the feces, in output waveforms acquired from the light-receiving pixels of the linear sensor,
the control section is configured to obtain the plurality of linear images from the linear sensor before the feces sink into the water-seal portion of the toilet bowl and when the feces pass through a light-output area for the illumination light to obtain reflected light components from the surface of the feces,
wherein a first linear image in the plurality of linear images is taken of a first region of the feces at a first time such that the first linear image does not include a second region of the feces, wherein the first linear image is taken in response to detection of a stimulus by one of: the linear sensor or another sensor communicatively coupled to the control section, and wherein a second linear image in the plurality of linear images is taken of the second region of the feces at a second time such that the second linear image does not include the first region of the feces, wherein the first time and the second time are a predetermined length of time apart.

2. The toilet seat according to claim 1, wherein the width direction is arranged perpendicular to a direction in which the feces are configured to fall.

* * * * *